United States Patent
Nilsson et al.

(10) Patent No.: US 9,295,833 B2
(45) Date of Patent: Mar. 29, 2016

(54) IMPLANTABLE MEDICAL LEAD

(75) Inventors: Kenth Nilsson, Åkersberga (SE);
Anna-Karin Johansson, Vallentuna (SE); Tom Eriksson, Uppsala (SE)

(73) Assignee: St. Jude Medical, AB, Jarfalla (SE)

( * ) Notice: Subject to any disclaimer, the term of this patent is extended or adjusted under 35 U.S.C. 154(b) by 2461 days.

(21) Appl. No.: 11/914,050

(22) PCT Filed: May 31, 2005

(86) PCT No.: PCT/SE2005/000829
§ 371 (c)(1),
(2), (4) Date: Sep. 18, 2008

(87) PCT Pub. No.: WO2006/130056
PCT Pub. Date: Dec. 7, 2006

(65) Prior Publication Data
US 2009/0125090 A1    May 14, 2009

(51) Int. Cl.
*A61N 1/05*        (2006.01)
*A61N 1/365*       (2006.01)

(52) U.S. Cl.
CPC .......... *A61N 1/056* (2013.01); *A61N 1/36564* (2013.01)

(58) Field of Classification Search
USPC ............ 607/1–2, 36, 63, 115–116, 119, 123; 600/372–374, 377
See application file for complete search history.

(56) References Cited

U.S. PATENT DOCUMENTS

| | | | |
|---|---|---|---|
| 4,033,355 A | 7/1977 | Amundson | |
| 5,330,520 A | 7/1994 | Maddison et al. | |
| 5,609,622 A * | 3/1997 | Soukup et al. | 607/122 |
| 5,681,514 A | 10/1997 | Woody | |
| 5,836,946 A | 11/1998 | Diaz et al. | |
| 6,564,107 B1 | 5/2003 | Bodner et al. | |
| 6,792,309 B1 * | 9/2004 | Noren | 607/23 |
| 2003/0181966 A1 | 9/2003 | Morgan | |
| 2004/0068313 A1 | 4/2004 | Jenney et al. | |
| 2004/0215300 A1 | 10/2004 | Verness | |

FOREIGN PATENT DOCUMENTS

WO    WO 02/34130    5/2002

* cited by examiner

*Primary Examiner* — Deborah Malamud

(57) ABSTRACT

An implantable lead for sensing mechanical activity of a human heart has an insulating polymeric tube extending from a proximal end to a distal end of the lead, an electrical conductor provided in the lumen of the polymeric tube, and a sensor connected to the conductor at the distal end thereof. The polymeric tube is provided with a conductive surface layer along the inner face between the polymeric tube and the electrical conductor, the conductive surface layer being in electrical contact with this conductor. Accumulation of electrical charges between the electric conductor and the polymeric tube is thereby prevented.

22 Claims, 3 Drawing Sheets

IMPLANTABLE MEDICAL LEAD

BACKGROUND OF THE INVENTION

1. Field of the Invention

The present invention generally relates to the field of implantable medical devices. More specifically, the present invention relates to an implantable lead for sensing mechanical activity of a human heart, the lead comprising a first non-conductive polymeric tube extending from a proximal end to a distal end of said lead, a first conductor provided in a lumen of said first polymeric tube, and a sensor.

2. Description of the Prior Art

Within the field of implantable medical devices, such as cardiac stimulators, cardioverters and defibrillators, different types of sensors have long been used for sensing and monitoring mechanical and electrical characteristics of the human heart. For instance, piezo-resistive, piezocapacitive or piezoelectric sensors could be used for sensing mechanical properties, such as pressure changes in the heart or in other blood vessels.

One example of a piezoelectric sensor suitable for use as a pressure sensor is shown in WO 02/34130. By using a pressure sensor in the heart, tachycardias, such as fibrillation, can be detected and also distinguished. Atrial fibrillation can be separated from ventricular fibrillation and electrical activity can be separated from mechanical activity. This is of importance for controlling the type of stimulation therapy to be delivered by a heart stimulator.

Furthermore, ever since the introduction of rate responsive implanted cardiac stimulators, a number of different parameters have been used for determining the activity level of the patient, which in turn is used for controlling the rate at which the heart of a patient is to be stimulated by the pacemaker. One of the most common sensors used is the piezoelectric accelerometer.

Unlike piezoresistive and piezocapacitive sensors, piezoelectric sensors are advantageous in that they are not energy consuming. Piezoelectric sensors are arranged to alter the mechanical stress of the piezoelectric material in response to a change of loads emanating from for instance an acceleration of a seismic mass or from a change in pressure acting on the sensor. This results in a transport of electrons or electrical charges within the material, which provides a change in voltage across the piezoelectric sensor. This voltage corresponds to the load to which the sensor is subjected. Thus, by monitoring the voltage changes across the piezoelectric sensor, changes for instance in pressure acting on the sensor can be monitored.

However, when using a piezoelectric sensor, such as a pressure sensor or an accelerometer, within a chamber of the heart or a blood vessel, measurements have shown that the voltage signal produced by the sensor is affected by motion artifacts. Such motion artifacts can be due to movements of the patient, i.e. jumping, running, etc., or the motions of the heart and the thorax during their regular cardiovascular operation. The motion artifacts could be large enough to disturb a sensor signal, especially when using a piezoelectric pressure sensor since the voltage changes produced by the piezoelectric sensor from pressure changes are very small. Furthermore, it could be difficult to separate the contribution of the motion artifacts from the useful signal contribution from pressure changes. Thus, depending on the contribution from the motion artifacts and the magnitude of the useful contribution to the pressure signal, the interpretation of the sensor signal could be rendered difficult or even impossible.

SUMMARY OF THE INVENTION

An object of the present invention is to provide a solution to the abovementioned problem of the detrimental contribution from motion artifacts to sensor signals.

The above object is achieved in accordance with the present invention by an implantable lead for sensing mechanical activity of a human heart having a first non-conductive polymeric tube extending from a proximal end to a distal end of the lead, a first conductor provided in a lumen of the first polymeric tube, and a sensor connected to the first conductor at a distal end thereof. Furthermore, the first polymeric tube is provided with a conductive inner surface layer, so as to prevent accumulation of electrical charges between said first conductor and said first polymeric tube.

Thus, the present invention is based on the advantageous idea of providing the cardiac lead connecting an intracardiac sensor to an implantable medical device, such as a cardiac stimulator, with electrically insulating tubing having an electrically conductive surface layer facing and contacting the conductor. By configuring the cardiac lead in such a manner, it has surprisingly been found that the contribution of motion artifacts to the sensor signal is greatly reduced. Thus, the effect of the motion artifacts is reduced to such an extent, that the contribution thereof to the sensor signal can be easily separated from the contribution of the characteristics, e.g. pressure changes, which the sensor is arranged to detect and measure.

When using a sensor in which changes in the sensed properties, e.g. pressure, give rise to small changes in voltage across the sensor, a charge amplifier operates to maintain the voltage across the sensor at a constant level, e.g. at 0 V, by receiving the electrical charges emitted by the sensor. As a result, the charge amplifier produces a voltage signal which is directly dependent on the amount of charges received from the sensor. In a cardiac stimulator, such a charge amplifier is positioned within the housing or the can of the cardiac stimulator, and a cardiac lead connects the sensor to the housing and the charge amplifier. Thereby, the voltage which the charge amplifier maintains at a constant level is that provided over the sensor and the conductor or conductors connecting the sensor to the charge amplifier. In a one conductor system, the sensor is connected between the conductor and ground, and in a two conductor system, the sensor is connected in series with the two conductors contained within the cardiac lead. Thus, the charge amplifier produces a voltage signal resulting from the transport of charges over the sensor, as well as any accumulation of electrical charges in the single conductor, or in the two conductors.

It should be noted that in the single conductor system, the sensor in a sense is still connected in series to the charge amplifier. However, for the single conductor system, it is an electrically conducting portion of the stimulator housing that is electrically connected to the charge amplifier. The sensor is then connected, on the one hand, to the conductor within the cardiac lead, and, on the other hand, to the stimulator housing via human tissue and blood surrounding the sensor and the stimulator. Thus, the tissue and blood acts as a conductor between the charge amplifier and the sensor.

By providing the surface of the tubing facing and contacting the conductor, in the one conductor system, or the conductors, in the two conductor system with an electrically conducting layer, there will be essentially no accumulation of electrical charges along the conductors. It has surprisingly been found that the contribution of motion artifacts to the sensor signal is greatly reduced and virtually eliminated, as described above.

According to the embodiments of the invention which involve a one conductor system, the cardiac lead comprises a conductor arranged within the lumen of a polymeric tube, which covers the conductor from end to end and provides electrical insulation of the conductor, in particular from surrounding tissue. In this embodiment, the inner surface of the tube which is in contact with the conductor is provided with an electrically conductive layer, such that the conductor is not in direct contact with the electrically insulating portions of the tube. Furthermore, the conductor is preferably helically wound within the polymeric tube.

According to the embodiments of the invention which involve a two conductor system, the cardiac lead comprises a second conductor arranged around the first polymeric tube, such that the first polymeric tube provides electric insulation between the two conductors. In this embodiment, the conductors and the first tube is arranged within the lumen of a second polymeric tube which is provided for covering both conductors and the first tube, and for providing electrical insulation of the conductors, in particular from surrounding tissue. Thus, the conductors and the polymeric tubes are preferably co-axially arranged. Furthermore, each conductor is preferably helically wound within the respective tube.

In the above mentioned two conductor embodiment, in addition to the inner surface layer of the first, inner tube being provided with an electrically conductive surface layer, the outer surface thereof, i.e. facing and contacting the outer conductor, is preferably provided with an electrically conductive surface layer. Furthermore, the inner surface of the second, outer tube, i.e. also facing and contacting the outer conductor, is preferably provided with an electrically conductive surface layer. Thus, in the most preferred embodiment of the invention in relation to a two conductor system, all surfaces of the polymeric tube in contact with the two conductors are provided with electrically conductive surface layers. Thus, no portion of the conductors are in direct contact with an electrically insulating portion of the polymeric tube, and there will be no accumulation of electrical charges due to motion artifacts along the interfaces between the conductors and the tube.

According to further embodiments of the invention involving one or two conductor systems, the polymeric tubing is in the form of a single tube provided with a plurality of longitudinally extending conductor lumina or lumens with axes arranged in parallel, each lumen being arranged for covering and electrically insulating a conductor. In these embodiments, the surface of each lumen facing and contacting a conductor connected to a sensor is provided with an electrically conductive surface layer. Preferably, the multiple lumina are arranged at the same diameter of the lead, circumferentially spaced apart at regular angular intervals. In addition, a centrally arranged lumen can be provided, i.e. running along the axial centre of the cardiac lead. A single lead preferably comprises two to four circumferentially spaced lumina, and one centrally arranged lumen. Furthermore, the conductors contained in each lumen are preferably not helically wound, but rather in the form of essentially straight, multi strand wires.

Other examples of tubes having a plurality of parallel lumina are also contemplated within the scope of the present application, for instance lumina having different diameters within the same tubing, having noncircular cross-sections, or being provided at different diameters within a single tubing. For instance, a tubing could be provided with two smaller and one larger lumina, wherein none of the axes the lumina coincides with the axis of the tubing.

It should be noted that the distinction made herein between one conductor systems and two conductor systems only refers to the number of conductors connecting a sensor to electronic circuitry within a housing of a medical implant. Thus, a lead for a one conductor system or for a two conductor system could be provided with further conductors that are not connected to a sensor.

In the following, different methods for providing the polymeric tubes or tubing with a conductive surface layer will be described. Also, there will be mentioned different materials suitable for providing the desired conducting properties. It should be noted, however, that although particular methods will be described, the present invention is not restricted to these methods or materials. On the contrary, and as readily realized by the skilled person, any method or material suitable for providing the polymeric tubing with a conductive surface layer is contemplated within the scope of the present invention.

In an embodiment, the polymeric tubing is a co-extrusion of a non-conductive, insulating portion and at least one conductive surface layer portion. The insulating portion and the conducting portion or portions are co-axially arranged. Furthermore, there is either one conducting portion which constitutes an inner surface layer or an outer surface layer, or two conducting portions which constitute an inner and an outer surface layer, depending on the particular embodiment.

In this example, the conductive portion of the coextrusion could be provided by mixing an electrically conductive powder or the like in a polymeric material, thus co-extruded. Such a powder could comprise a metal, preferably a biocompatible metal, such as titanium, platinum, gold, niobium, iridium, ruthenium, tungsten, zirconium, or tantalum, or alloys thereof, or conductive metal oxides or nitrides, such as titanium nitride. Other examples include carbonaceous materials, such as graphite, coke, soot, or compounds of carbon intercalated with alkali metals, such as lithium or potassium.

Furthermore, the insulating polymer could be co-extruded with another, electrically conductive polymer, which makes up the conductive surface portions of the tubing. Examples of conducting polymers include polyacetonitrile (PAN), and poly-mercaptanes. The conductive polymer can be a polymer having conjugated double bonds, or aromatic rings, that permit transport of electrons through the polymer, thereby rendering the polymer conductive, possibly with the further addition of a suitable dopant, such as polypyrrole, polyanitine, or polythiophene. Other examples of conductive polymers include a non-conductive polymeric matrix provided with a conductive filler material.

In another embodiment, a polymeric, insulating tubing is provided with at least one electrically conducting coating constituting the respective electrically conductive surface layer. Such a coating could be obtained by applying a solution comprising an electrically conductive material onto the tubing, for example by spraying the solution onto the surface of the polymeric tubing, submerging the polymeric tubing in the solution, etc. The solution could be a powder (see above for examples) in suspension, a conductive polymer in a solvent etc. As the solution dries, the conductive material adheres to the surface of the tubing, thereby providing said electrically conductive surface coating of the tubing. Further examples involve providing a coating by blowing an electrically conductive powder onto the surface of the tubing, by rubbing an electrically conducting material onto the tubing. Thereby, a tubing having an electrically conducting coating is formed. The conductive material could be mechanically worked into the surface of the tubing, such as by kneading or squeezing the tubing through a mangle. Optionally, the tubing could be expanded by swelling prior to applying the coating in order to enhance the adhesion between the coating and the surface of the tubing. Furthermore, the surface of the tubing could be heated after application of the coating in order to enhance the adhesion between the coating and the tubing. As readily understood by the person skilled in the art, several of the above-mentioned methods and method steps for providing the surface of the tubing with a conductive surface could be combined.

According to further embodiments of the present invention, the conductive surface layer of the polymeric tubing is further arranged to have a lubricating effect. Due to the continued efforts in decreasing the cross-section dimensions of cardiac leads, along with development of new materials for the polymeric tubing with increased adhering properties, cardiac leads become increasingly difficult to assemble. By providing the conductive surface layer of the polymeric tubing with lubricating properties, the frictional force between the polymeric tubing and the conductors could be significantly reduced.

Thereby, not only would the conductive surface layer reduce or eliminate the effects of motion artifacts on the sensor signal, the lubricating effect of the layer would also facilitate the assembly of the cardiac lead. According to one preferred embodiment, the surface layer of the tubing comprises graphite, which has both lubricating and conductive properties. However, other suitable materials having both lubricating and conducting properties could be used without departing from the scope of the present invention, in particular the carbonaceous materials mentioned herein.

BRIEF DESCRIPTION OF THE DRAWINGS

FIG. 2b is a transversal cross-section view of the electrode lead shown in FIG. 2a.

DESCRIPTION OF THE PREFERRED EMBODIMENTS

The following is a description of preferred embodiments in accordance with the present invention. This description is intended for describing the general principles of the invention and is not to be taken in a limiting sense. Thus, even though a biventricular heart stimulator for sensing and stimulating in both ventricles is being illustrated, the invention is also applicable to heart stimulators arranged for sensing and stimulating in one ventricle only, and/or for stimulating in the atria of a human heart. Furthermore, the invention is also applicable to implantable cardioverter-defibrillators (ICD).

Figure 1:
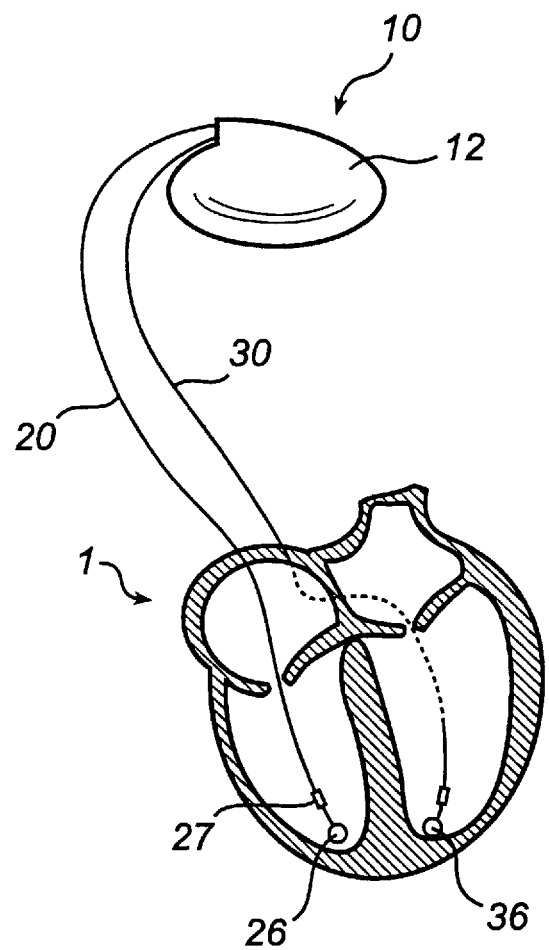
FIG. 1 is a simplified, partly cutaway view illustrating an implantable stimulation device in electrical communication via cardiac leads with a human heart.

Referring first to FIG. 1, there is shown an implantable heart stimulator 10 in electrical communication with a human heart 1 via two cardiac leads 20, 30 arranged for stimulation and sensing. Moreover, the heart stimulator 10 comprises electronic circuitry and a battery contained within a hermetically sealed pacemaker housing 12. The housing 12 has a metallic casing of titanium, enclosing the electronic circuitry and battery, and a molded plastic header, comprising connector blocks and apertures for receiving the connectors at the proximal ends of the cardiac leads. The header is attached to the metallic casing in a fixed and sealed arrangement.

The electronic circuitry comprises at least one pulse generator for generating stimulation pulses, sensing circuitry for receiving cardiac signals sensed by the cardiac leads 20, 30, and a controller. The controller controls both the sensing of cardiac signals and the delivery of stimulation pulses, for instance as to the duration, energy content and timing of the stimulation pulses.

The stimulation pulses generated by the pulse generator are transmitted via the cardiac leads 20, 30 and delivered to the cardiac tissue of the left and right ventricles of the heart, respectively, by the use of tip electrodes 26, 36. Generally, the tip electrode 26, 36 acts as the cathode when the cardiac pulse is delivered. Furthermore, in unipolar cardiac systems, the casing 12 acts as the anode, while in bipolar cardiac systems, the anode is provided by an annular electrode (not shown) arranged on the cardiac lead at a small distance from the tip electrode. It should be noted that even though no annular or ring electrode is illustrated in the greatly simplified drawing of FIG. 1, the present invention is equally applicable to unipolar and bipolar systems.

Figure 2A:
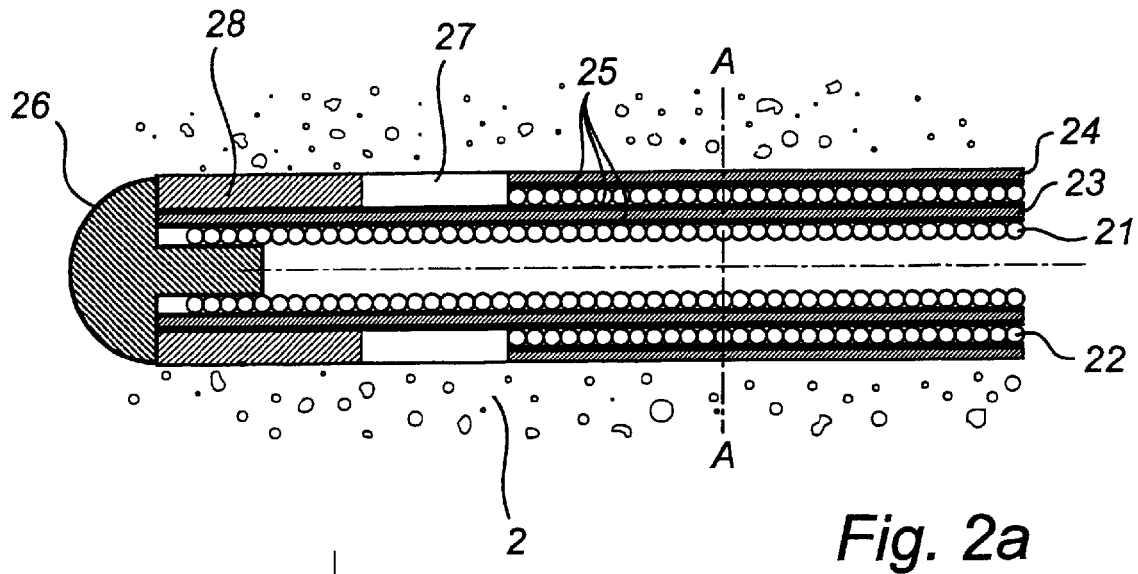
FIG. 2a is a longitudinal cross-section view of an electrode lead according to one embodiment of the invention.
Figure 2B:
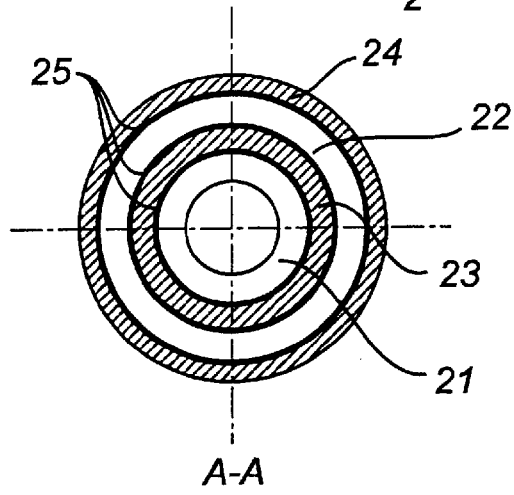

Turning now to FIGS. 2a and 2b, there is shown an implantable lead 20 in accordance with a preferred embodiment of the present invention. The lead 20 has an inner conductor 21 and an outer conductor 22, both in the form of helical coils. The inner conductor 21 is connected to the tip electrode 26 and the outer conductor 22 is connected to a piezoelectric pressure sensor 27, which will be described further below. The two conductors 21, 22 are coaxially arranged and separated by a flexible inner tubing 23 made of an electrically insulating polymeric material, which in the preferred embodiments is silicone rubber or polyurethane rubber (PUR). Thus, the conductors 21, 22 are completely separated and electrically insulated from each other. Furthermore, an outer tubing 24 is co-axially arranged about the outer conductor 22 for separating and insulating the outer conductor 22 from surrounding tissue 2, generally blood. Furthermore, an electrically insulating sleeve 28 is arranged between the sensor 27 and the tip electrode in order to provide the distal portion of the lead 20 with a uniform diameter. In this embodiment, the outer tubing 24 and the distal sleeve 28 is also made of silicone rubber or PUR.

Moreover, the surfaces of the inner tubing 23 and the outer tubing 24 facing the inner and outer conductors 21, 22, respectively, are provided with electrically conductive surface layers 25. Thereby, no portions of the conductors 21, 22 are in direct contact with the electrically insulating portions of the tubing 23, 24, and there will be no accumulation of electrical charges due to motion artifacts between the conductors 21, 22 and the tubes 23, 24.

In one preferred embodiment, the electrically conducting layers 25 are provided by coating the corresponding surfaces of the polymeric tubing 23, 24 with graphite. The graphite layer is provided as a graphite powder. The graphite layers 25 are provided prior to assembling the cardiac lead. In addition to the graphite providing the tubing 23, 24 with electrically conductive surfaces, the graphite also has lubricant properties. Thereby, the friction between the tubing 23, 24 and the conductors 21, 22 is reduced, which inter alia facilitates the assembly of the cardiac lead 20, in particular when the conductors are fed into and through the lumen of the cardiac lead during assembly thereof.

As noted above, in the embodiment shown in FIGS. 2a and 2b, the cardiac lead 20 has two helically wound conductors 21, 22. However, even though the lead comprises dual conductors, the lead 20 is a unipolar lead. This is due to the fact that the term "unipolar" only refers to the electrodes or "poles" that are being used for the delivery of cardiac pulses. In the present embodiment, the outer conductor 22 is arranged for transmitting electrical signals between the pressure sensor 27 and the heart stimulator 10, and not for delivering stimulation pulses to an electrode positioned in the human heart. Accordingly, in the presently described embodiment, there is only one stimulating electrode 26 located in the human heart and the disclosed lead is a unipolar lead. However, the invention is of course not limited to unipolar leads. On the contrary, the cardiac lead could be provided with further conductors connected to further sensors and/or stimulating electrodes. In particular, a further conductor connected to a ring electrode provided for delivering stimulation pulses is contemplated.

The pressure sensor 27 is coaxially arranged about the inner tubing 23 distally of the outer conductor 22, which is connected to the sensor 27 via a sensor electrode (not shown) provided on the sensor. In this embodiment, the sensor 27 is a piezoelectric pressure sensor of the type shown in the International application published under No. WO 02/34130, which hereby is incorporated herein by reference. The sensor 27 comprises a piezoelectric element disposed coaxially around a rigid supporting structure. Changes in pressure acting on the piezoelectric sensor 27 results in transport of electrical charges across the sensor, which would cause small changes in the voltage across the sensor. However, since the sensor 27 is connected to a charge amplifier 14, contained within the stimulator housing 12, these charges are conducted to the charge amplifier 14. The charge amplifier 14 absorbs the charges and keeps the voltage across the sensor 27 constant. Furthermore, the charge amplifier 14 outputs a voltage signal corresponding to the transported charges. Thus, in order for the transport of electrical charges across the sensor 27 to be transmitted to the charge amplifier, two conductors, electrically insulated from each other, are connected to electrodes provided on the sensor and to the inputs of the voltage amplifier.

A first electrode (not shown) of the sensor is connected to the outer conductor 22 of the cardiac lead 20. Furthermore, a second electrode (not shown) of the sensor 27 is electrically connected via the sleeve 28 to the tip electrode 26, and thereby to the inner conductor 21. Thus, the inner conductor 21 is arranged for transmitting stimulation pulses from the stimulator 10 to the tip electrode 26, as well as for transmitting electrical signals from the sensor 27 to the stimulator 10. In this embodiment, the sleeve 28 is provided with an electrical conductor, connecting the tip electrode with the sensor electrode, and insulated from the surrounding tissue. Also, the sensor 27 is provided with an outer silicone rubber layer in order to insulate the sensor 27 from the surrounding tissue 2, in particular the electrodes of the sensor 27. This embodiment will be further described below in relation to FIG. 5.

However, in an alternative embodiment, the sensor 27 is in direct contact with the surrounding blood or tissue 2. Thus, the second electrode (not shown) is provided on the circumference of the sensor 27 such that an electrical contact with the metal casing of the stimulator housing 12 is established via the surrounding tissue. Then, there is no need for providing the sleeve 28 with an electrical conductor. Accordingly, the sleeve 28 is merely made in an insulating material, ensuring that there is no electrical connection between the sensor 27 and the tip electrode 26. As readily understood by the person skilled in the art, such a circumferential electrode facing the surrounding tissue must be provided in a material which is biocompatible. This embodiment will be further described below in relation to FIG. 4.

Figure 3:
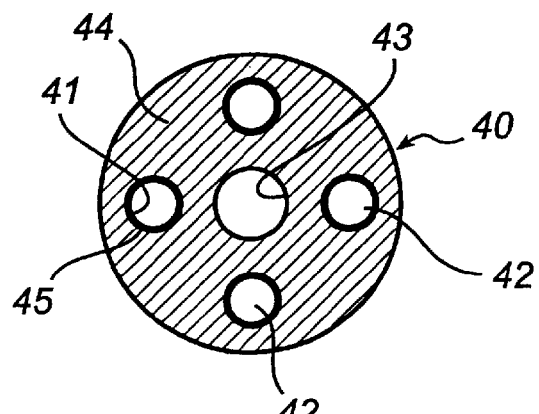
FIG. 3 is a transversal cross-section view of an electrode lead according to a further embodiment of the invention.

Turning now to FIG. 3, there is illustrated a cardiac lead 40 according to an alternative embodiment of the present invention. In this embodiment, the cardiac lead 40 comprises a silicone rubber tubing 44 provided with a plurality of circumferentially spaced lumina 41, as well as a central lumen 43 arranged at the axial centre of the lead 40. The central lumen 43 is arranged for receiving a guide wire or stylet, which is used for guiding and controlling the cardiac lead during implantation thereof. Following implantation, the guide wire is removed from the cardiac lead. Alternatively, one of the circumferentially arranged lumina 41 could be used for receiving a guide wire.

In the shown embodiment, conductors 42 are provided within the circumferentially arranged lumina 41, wherein two of the conductors 42 are connected to a pressure sensor 27. In the same manner as is described above in relation to FIGS. 2a and 2b, the surfaces of the lumina 41 are provided with electrically conducting surface layers 45. In the preferred embodiments, the surface layers 45 are provided by coating the tubing surfaces with graphite. Thereby, the friction between the conductors 42 and the tubing 44 is reduced and assembly of the lead is facilitated in the manner as described above.

Figure 4:
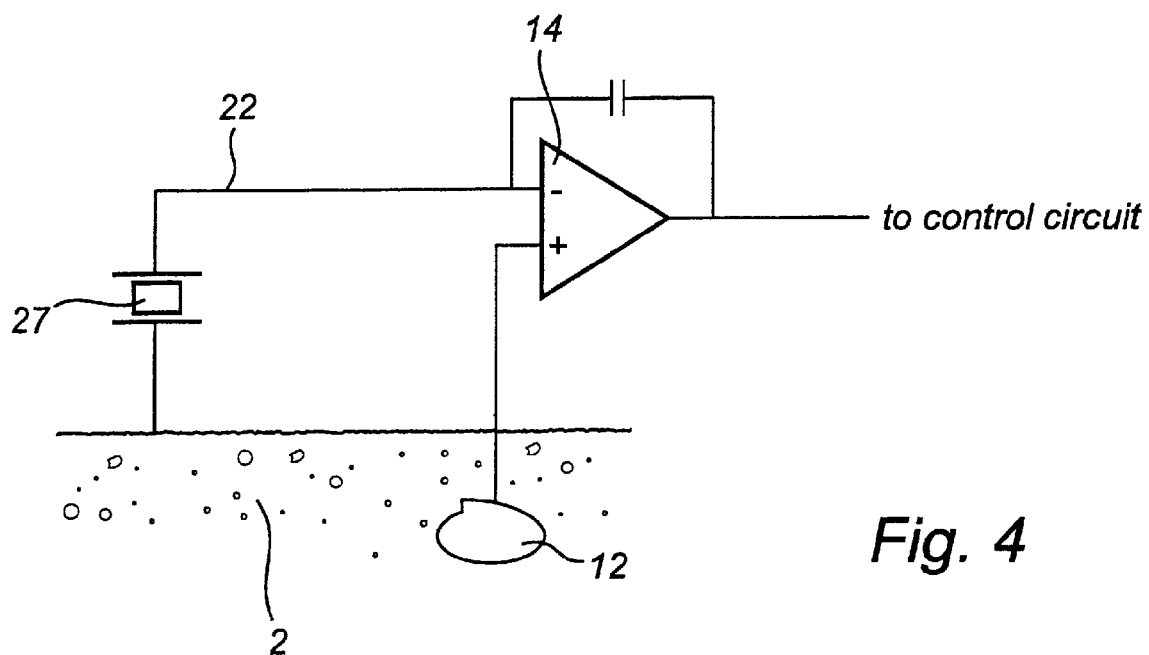
FIG. 4 is a schematical circuit diagram illustrating a system wherein a sensor is connected to a charge amplifier via one conductor in the electronic lead.
Figure 5:
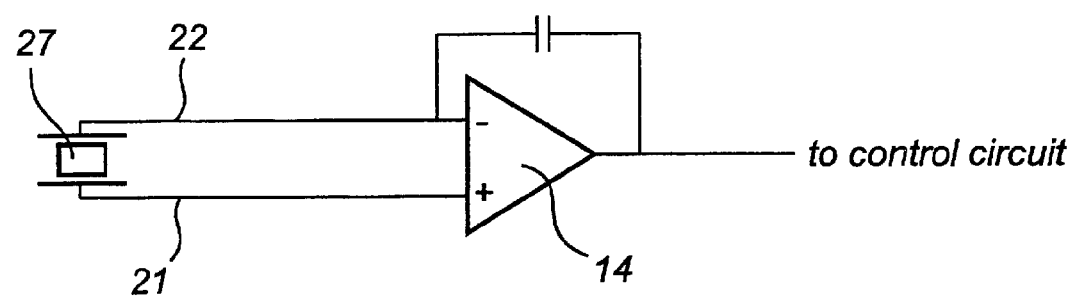
FIG. 5 is a schematical circuit diagram illustrating an alternative system with a sensor connected to a charge amplifier via two conductors within the electronic lead.

Turning now to FIGS. 4 and 5, there is illustrated in simplified form a circuit diagram of the charge amplifier and the sensor. First, a single conductor system is shown in FIG. 4. The system comprises a piezoelectric pressure sensor 27, a conductor 22 located within a cardiac lead, and a charge amplifier 14. One input of the charge amplifier 14 is connected via the conductor 22 to a first electrode of the sensor 27. Furthermore, the other input of the charge amplifier 14 is connected to a second electrode of the sensor 27, via a metallic, electrically conducting portion of the stimulator housing 12 and intervening blood and tissue. Thus, the respective inputs to the charge amplifier 14 are connected across the sensor 27. Thereby, changes in pressure acting upon the sensor results in transport of electrical charges across the sensor 27. The charge amplifier 14 receives the transported charges, maintains the voltage across the sensor at a constant level, and outputs an amplified voltage signal corresponding to the transport of charges and variations in pressure to control circuitry.

With reference to FIG. 5, a two conductor system is illustrated. This system corresponds to the system illustrated in FIG. 4, except for the fact that the inputs of the charge amplifier 14 are both connected to the sensor 27 via conductors 21, 22, respectively, located within the cardiac lead. Thus, the charge amplifier 14 operates in similar manner to output a voltage signal corresponding to pressure changes acting on the piezoelectric pressure sensor 27.

It should be noted that even though the present invention has been described above in relation to exemplifying embodiments thereof, alterations and modifications may be made within the scope of the invention, as defined in the accompanying claims. For instance, the invention is not restricted to a specific method of providing the polymeric tubes or tubing with an electrically conductive surface layer. A variety of different suitable methods could be used, depending on the chosen conducting material, as understood by the person skilled in the art. Furthermore, different methods could be used for different surfaces. For instance, one method could be most appropriate for the inner surface layers, while another method is more appropriate for the outer surface layers.

Likewise, the material for providing the electrical conductivity of the surface layers is by no means limited to graphite. A variety of suitable materials are contemplated within the scope of the present invention. Moreover, different materials could be used for the different surfaces within the same cardiac lead.

Although modifications and changes may be suggested by those skilled in the art, it is the intention of the inventors to embody within the patent warranted heron all changes and modifications as reasonably and properly come within the scope of their contribution to the art.

We claim as our invention:

1. An implantable lead for sensing activity of a human heart, comprising:
   a non-conductive polymeric tube extending from a proximal end to a distal end of said lead;
   a conductor provided in a lumen of said polymeric tube, said lumen having an inner surface facing said conductor;
   a sensor connected to said conductor at a distal end thereof; and
   said polymeric tube having a conductive inner surface layer on said inner surface of said lumen, in electrical contact with said conductor, that prevents accumulation of electrical charges between said conductor and said polymeric tube.

2. The lead as claimed in claim 1, wherein said polymeric tube is a first polymeric tube and said conductor is a first conductor, and said lead further comprising a second conductor around said first polymeric tube, said sensor being connected to said second conductor at a distal end thereof, and a second non-conductive polymeric tube extending from a proximal end to a distal end of said lead, said second polymeric tube also being around said second conductor.

3. The lead as claimed in claim 2, wherein said first polymeric tube has a conductive outer surface layer, that prevents accumulation of electrical charges between said second conductor and said first polymeric tube.

4. The lead as claimed in claim 2, wherein said second polymeric tube has a conductive inner surface layer, that prevents accumulation of electrical charges between said second conductor and said second polymeric tube.

5. The lead as claimed in claim 2, wherein said second polymeric tube has a conductive outer surface layer, said outer surface layer being configured for exposure to human tissue surrounding the lead during and following implantation.

6. The lead as claimed in claim 2, wherein said second conductor is helically wound around said first polymeric tube.

7. The lead as claimed in claim 2, wherein said sensor is a piezoelectric sensor electrically connected to at least one of said first conductor and said second conductor.

8. The lead as claimed in claim 1, wherein said polymeric tube has an outer surface with a conductive outer surface layer thereon, said outer surface layer being configured for exposure to human tissue surrounding the lead during and following implantation.

9. The lead as claimed in claim 1, wherein said conductor is helically wound inside said polymeric tube.

10. The lead as claimed in claim 1 wherein said conductor is a first conductor and, wherein said polymeric tube comprises a plurality of longitudinally extending parallel lumina, and said lead further comprising a second conductor;
    said first conductor being in a first lumen and said second conductor being in a second lumen of said plurality of lumina; and
    at least said first lumen and said second lumen each having an inner surface with a conductive inner surface layer thereon, that prevents accumulation of electrical charges between said first conductor and said second conductor, respectively, and said polymeric tube.

11. The lead as claimed in claim 1, wherein said conductive surface layer is a coating on the inner surface of said lumen, said coating comprising at least one electrically conductive material.

12. The lead as claimed in claim 1, wherein said conductive surface has at least one electrically conductive material, said layer being co-extruded with said polymeric tube.

13. The lead as claimed in claim 11, wherein said electrically conductive material comprises at least one carbon-containing conductive material.

14. The lead as claimed in claim 13, wherein said at least one carbon-containing conductive material is selected from the group consisting of graphite, a graphite-like carbon material, coke or soot.

15. The lead as claimed in claim 13, wherein said at least one carbon-containing conductive material is an intercalation compound comprising an alkali metal.

16. The lead as claimed in claim 15 wherein said alkali metal is selected from the group consisting of lithium and potassium.

17. The lead as claimed in claim 11, wherein said at least one electrically conductive material comprises at least one of a metal or an electrically conductive metal oxide.

18. The lead as claimed in claim 17, wherein said at least one electrically conductive material is in the form of a powder.

19. The lead as claimed in claim 18 wherein said at least one electrically conducted material is a powder mixed with a non-conductive polymer.

20. The lead as claimed in claim 11, wherein said at least one electrically conductive material comprises an electrically conductive polymer.

21. The lead as claimed in claim 1, wherein said conductive surface layer has a lubricating effect that reduces friction between said polymeric tube and said conductor.

22. The lead as claimed in claim 1 wherein said sensor is a piezoelectric sensor.

* * * * *